(12) United States Patent
Reignier et al.

(10) Patent No.: US 9,089,441 B2
(45) Date of Patent: Jul. 28, 2015

(54) TRIAL INSTRUMENT ASSEMBLY FOR USE IN A SURGICAL PROCEDURE

(75) Inventors: Carole Reignier, Lyons (FR); Laurent Zanchin, Mions (FR)

(73) Assignee: DEPUY (IRELAND) (IE)

( * ) Notice: Subject to any disclaimer, the term of this patent is extended or adjusted under 35 U.S.C. 154(b) by 312 days.

(21) Appl. No.: 13/483,825

(22) Filed: May 30, 2012

(65) Prior Publication Data

US 2013/0325132 A1 Dec. 5, 2013

(51) Int. Cl.
*A61B 17/58* (2006.01)
*A61B 17/60* (2006.01)
*A61F 2/00* (2006.01)
*A61F 2/46* (2006.01)
*A61F 2/36* (2006.01)

(52) U.S. Cl.
CPC ............. *A61F 2/4684* (2013.01); *A61F 2/3609* (2013.01)

(58) Field of Classification Search
USPC .............................................. 606/96–98, 102
See application file for complete search history.

(56) References Cited

U.S. PATENT DOCUMENTS 5,607,431 A * 3/1997 Dudasik et al. ................. 606/80
5,792,143 A 8/1998 Samuelson

* cited by examiner

*Primary Examiner* — Sameh Boles

(57) ABSTRACT

A trial instrument assembly for use in a surgical procedure to replace an orthopaedic joint includes a trial implant having a stem portion for fitting within a prepared cavity in the patient's bone. The stem portion defines a stem axis. A neck portion is connected to the stem portion to protrude from the cavity when the stem portion is within the cavity. The assembly includes a plane guide that extends from the neck portion in a plane that is selected from (i) a plane perpendicular to the stem axis, and (ii) a plane parallel to the stem axis, for use in determining the location of the trial implant relative to an anatomical feature in a direction measured along the stem axis or perpendicular to the stem axis, respectively.

13 Claims, 3 Drawing Sheets

TRIAL INSTRUMENT ASSEMBLY FOR USE IN A SURGICAL PROCEDURE

BACKGROUND TO THE INVENTION

This invention relates to a trial instrument assembly for use in a surgical procedure to replace an orthopaedic joint and to a method of preparing a bone to receive an implant component in such a surgical procedure.

The success of an operation to replace an orthopaedic joint with a joint prosthesis depends on factors that include: (i) selection of appropriate joint prosthesis components; and (ii) accurate preparation of the bone so that the selected prosthesis components are properly located relative to one another and to features of the patient's bone structure. These factors can affect the fit of the prosthesis components in the patient's bone. These factors can also affect the articulation of the joint prosthesis after implantation, in particular as to whether the articulation of the implanted joint prosthesis accurately reproduces that of the patient's healthy natural joint or some other sought joint construction.

A surgeon can make use of images of the patient's bones in a pre-operative planning stage to identify appropriate prosthesis components that will be appropriate to match a patient's anatomy. The planning stage can also include identifying details of steps in the preparation of the patient's bone to receive the selected prosthesis components.

It is normal to check the fit of a selected prosthesis component in a cavity in a prepared bone. This can be done using a trial component that has a shape similar to that of the ultimate implant component which is to be implanted.

SUMMARY OF THE INVENTION

The present invention provides a trial implant that provides a plurality of tongues or grooves that can be engaged by a plane guide which, when so engaged, extends beyond the trial implant allowing the position of the trial implant relative to an adjacent anatomical feature to be assessed.

Accordingly, the invention provides a trial instrument assembly for use in a surgical procedure to replace an orthopaedic joint, the assembly comprising:

a. a trial implant having a body portion for fitting within a prepared cavity in the patient's bone and a guide portion that is connected to the body portion to protrude from the cavity when the body portion is within the cavity, the guide portion providing at least one first part of a projection and recess assembly, and b. a plane guide having a first portion that provides the second part of the projection and recess assembly and engages the first part of the assembly provided by the guide portion of the trial implant to connect the plane guide with the trial implant, and a second portion that, when the second part of the projection and recess assembly provided by the first portion of the plane guide, is engaged with the first part of the assembly provided by the guide portion of the trial implant, and extends beyond the end of the second part of the assembly where it engages the first part of the assembly.

The invention also provides a trial instrument assembly for use in a surgical procedure to replace an orthopaedic joint, the assembly comprising:

a. a trial implant having a stem portion for fitting within a prepared cavity in the patient's bone, the stem portion defining a stem axis, and a neck portion which is connected to the stem portion to protrude from the cavity when the stem portion is within the cavity, and b. a plane guide which extends from the neck portion in a plane that is selected from (i) perpendicular to the stem axis, and (ii) parallel to the stem axis, to determine the location of the trial implant relative to an anatomical feature in a direction that is measured along the stem axis or perpendicular to the stem axis, respectively.

The plane guide can be fixed to the trial implant. When the plane guide is fixed to the trial implant, the trial implant can be provided as one of a set that differ from one another in one or more dimensions so that they correspond to different sizes of implant component. The plane guide can be fixed to a guide portion of the trial implant that can be separated from the stem portion thereof.

Alternatively, the plane guide can be fastened to the trial implant in such a way that it can be separated from the trial implant. The plane guide can be fastened to the trial implant such that it can be moved relative to the trial implant along an axis parallel to the stem axis (especially when the plane guide extends from the neck portion in a direction that is perpendicular to the stem axis), or along an axis perpendicular to the stem axis (especially when the plane guide extends from the neck portion in a direction parallel to the stem axis).

The invention also provides a method of preparing a bone to receive an implant component in a surgical procedure to replace an orthopaedic joint, the method making use of the assembly of the invention and comprising:

a. positioning the body portion of the trial implant in a prepared cavity in the patient's bone, b. engaging the parts of the projection and recess assembly provided by the first portion of the plane guide and the guide portion of the trial implant, so that the second portion of the plane guide extends beyond the trial implant, c. assessing the position of the second portion of the plane guide relative to an adjacent anatomical feature.

The invention enables the surgeon to assess the location of the trial implant relative adjacent anatomical features. This information can be used by the surgeon to ensure that appropriate implant components are selected to suit the patient's anatomy, for example in terms of length, width, offset, version angle, and other variables that are available to a surgeon when selecting components to suit a particular patient's anatomy. The information can also be used by the surgeon to determine whether a cavity in a patient's bone has been prepared appropriately to ensure that a selected prosthesis component is appropriately located in the bone relative to other anatomical features.

The body and guide portions of the trial implant can be provided as separate components that have formations by which the components can be connected to one another. For example, the formations can comprise at least one spigot provided on one of the components and a socket on the other of the components in which the spigot can be received. It can be preferred to provide two spigots and two corresponding sockets, with one spigot-and-socket pair spaced apart from the other spigot-and-socket pair. It can be preferred that each of the body and guide portions has a spigot from one spigot-and-socket pair and a socket from another spigot-and-socket pair.

The provision of a trial implant in which the body and guide portions are provided as separate components has the advantage that it allows the body portion to be fitted into a prepared cavity in the bone without the guide portion in place. This can facilitate manipulation of the body portion, for example using manipulator instruments as is known.

The provision of a trial implant in which the body and guide portions are provided as separate components also helps to reduce inventory, allowing different sizes of guide portions to be used with any body portion.

The assembly can include a trial neck component that can be fitted to the body portion of the trial implant in place of the guide portion of the trial implant. The method of the invention can then include the step of removing the guide portion of the trial implant from the body portion thereof, and fitting a trial neck component to the body portion of the trial implant in place of the guide portion thereof.

The recess and projection assembly facilitates the alignment of the trial implant and the plane guide where, when the projection is received in the recess, the body and guide portions of the trial implant are aligned, allowing the plane guide to be used to assess the position of the trial implant relative to an adjacent anatomical feature. In particular, the plane of the plane guide is fixed relative to the body part of the trial implant. The projection can be elongate so that it fits into a recess which is also elongate in the manner of a groove. In particular, the recess and projection assembly can be provided as a tongue and groove assembly. The projection might have a different configuration. For example, the projection could be provided as one or more pegs. Such pegs might fit into respective sockets. Such pegs might fit into one or more grooves. The use of one or more elongate recesses in the form of one or more grooves has the advantages of enabling the plane guide to slide relative to the trial implant without having to disconnect the plane guide from the trial implant completely, by allowing the projection (for example a tongue or one or more pegs) to slide within a groove in which it is received.

The guide portion of the trial implant can provide a plurality of first parts of a projection and recess assembly. When the guide portion provides more than one first part, it will frequently be preferred that all of them are projection parts or that all of them are recess parts.

The shape of the opposite walls of the recess (for example groove) will be selected so that the projection (for example tongue) is a snug fit in the recess. It will frequently be preferred that the opposite walls of the recess are approximately parallel, at least over most of the depth of the recess, to accommodate a projection which has a constant thickness. The recess can be shaped so as to retain a projection in the recess, for example by being tapered slightly especially at its inward edge which the projection is inserted towards.

Preferably a groove is open at least one of its ends. This can allow the projection (for example a tongue) to be slid freely relative to that end of the groove. This can facilitate positioning of the plane guide relative to the trial implant and to a feature of the patient's anatomy.

The projection should be a snug fit in the recess so that the second portion of the plane guide is substantially fixed relative to the first portion of the plane guide against movement out of the plane which is defined by the projection and recess assembly. It can be preferred that the parts of the projection and recess assembly that are provided on the trial implant are grooves and that the first portion of the plane guide defines a projection that is a snug fit in a selected one of the recesses. At least the first portion of the plane guide can be a plate that is a snug fit in the or each groove on the guide portion of the trial implant, the plate extending beyond the end of the groove.

The plane guide should be sufficiently rigid to ensure that it does not bend significantly especially in the second portion thereof where it extends beyond the end of the trial implant. This can be achieved by use of a plane guide which consists of a plate of a metal such as a stainless steel, especially having a thickness of at least about 0.5 mm.

The plane guide can be provided by a sheet of material whose thickness is selected so that the sheet is a snug fit in a groove on the guide portion of the trial implant. Accordingly, the thickness of the tongue that is provided by the body portion of the plane guide is the same as the thickness of the remainder of the sheet by which the plane guide is provided.

The body and guide portions of the trial implant can be made from the same material or from different materials. Materials that can be used to make the body and guide portions of the trial implant can include metals and polymeric materials. Examples of metals used in the manufacture of surgical instruments include certain stainless steels. Examples of polymeric materials used in the manufacture of surgical instruments include polyolefins, polycarbonates, PEEKs, polyamides, polyesters. Polymeric materials can be reinforced with fibrous material, especially carbon fibers. It can be preferred for the body portion of the trial implant to be made from a metal that can withstand the forces to which it is subjected when it is fitted in a prepared cavity in a bone. The guide portion of the trial implant can be made from a polymeric material. This has the advantage of ease of manufacture, for example by use of a molding technique.

The guide portion of the trial implant can provide two spaced-apart first parts of a projection and recess assembly that define first and second planes, the first plane being parallel to the second plane. The two planes can correspond to different sizes of a component of an implant assembly ultimately implanted in the patient. Alternatively, the two planes can correspond to different positions of a component of an implant assembly within a patient's bone.

The guide portion of the trial implant can provide two first parts of a projection and recess assembly which define first and second planes, the first plane being perpendicular to the second plane. The two planes can define respective planes for the plane guide to locate it relative to two different anatomical features.

The guide portion of the trial implant can provide combinations of one, two or more spaced-apart parts of a projection and recess assembly that define first planes that are parallel to one another and one, two or more spaced apart parts of a projection and recess assembly which define second planes that are perpendicular to the first planes.

The assembly of the invention can be used in procedures to replace parts of a joint or an entire joint. It can be used in procedures to replace all or parts of hip, shoulder, knee, ankle joints. For example, the body portion of the trial implant can be a stem trial for use in preparing the femur in a hip joint replacement procedure or for use in preparing the humerus in a shoulder joint replacement procedure.

The invention is particularly suitable for use in preparing a cavity in a femur to receive the femoral stem component of a hip joint. The body portion of the trial implant can be a stem trial that is configured to fit in a prepared cavity in the patient's bone to replicate the fit of an implant component in the cavity. The body portion of the trial implant can be used to prepare the cavity in the bone to receive the implant component in a subsequent step. For example, the body portion can have one or more cutting teeth on its external surface by which the cavity is shaped to receive the implant component. The body portion could also be used to compact the material on the surface of the cavity in a tamping step.

The guide portion of the trial implant can be mounted on the body portion. It can provide at least one projection or recess, preferably a pair of parallel projections or recesses, (for example tongues or grooves, especially grooves), arranged so that they extend in a plane that is approximately perpendicular to the superior-inferior axis, allowing the body portion of the trial implant to be located relative to the greater trochanter. The guide portion of the trial implant can have at least one projection and recess (for example tongue or groove, preferably at least one groove) that extends in a plane that is approximately perpendicular to the medial-lateral axis, allowing the body portion of the trial implant to be located relative to the lesser trochanter. The guide portion of the trial implant can be replaced by a neck trial. This can be appropriate once the step of locating the body portion of the trial implant has been completed. A trial head can be mounted on the trial neck for articulation relative to an acetabular bearing surface, provided by an implant component or trial or by the patient's natural tissue.

INTRODUCTION TO THE DRAWINGS

Embodiments of the invention are described below by way of example with reference to the accompanying drawings, in which.

DESCRIPTION OF PREFERRED EMBODIMENTS

Figure 1:
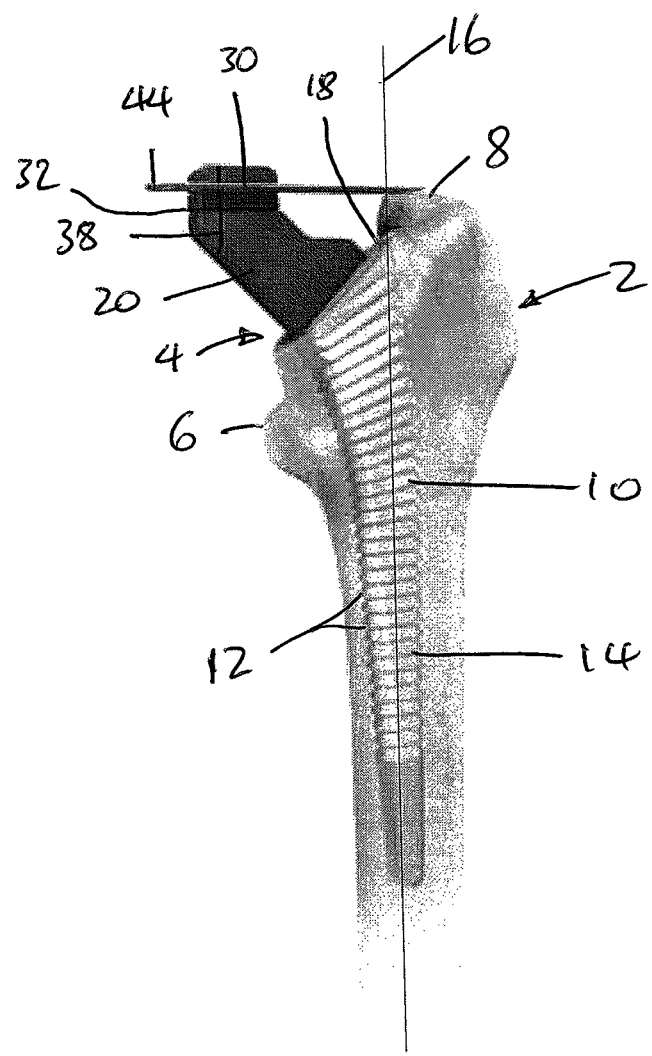
FIG. 1 is a side view of a proximal femur with a trial implant which comprises a stem located within the intramedullary cavity with a guide portion fitted to it.

Referring to the drawings, FIG. 1 shows the proximal portion of a femur 2 with a trial implant 4 located in a cavity within the femur. The femur has been prepared by steps used conventionally in hip replacement surgery. The assembly of the invention can be used in a surgical method of implanting a femoral component of a hip joint, as discussed in more detail below.

The trial implant is used to provide an indication of the location of a stem trial relative to adjacent anatomical landmarks such as the lesser trochanter 6, the trochanteric fossa and the greater trochanter 8.

The trial implant comprises a stem trial 10 that can be received in the prepared intramedullary cavity in proximal femur. The stem trial may have cutting teeth 12 on its outer surface so that it can be used as a broach to prepare the cavity to receive the stem trial, and subsequently the femoral component of a hip joint prosthesis. The cutting teeth on the stem trial mean that it can be used in steps that cut the bone surface to shape the cavity and to compact the bone tissue that defines the cavity.

The distal portion 14 of the stem trial 10 that is received in the diaphyseal region of the femur defines a stem axis 16 that is aligned with the femoral axis when the stem trial is received in the intramedullary femoral cavity. The stem trial has a neck surface 18 that extends at angle of about 45° to the stem axis.

The stem trial 10 is formed from stainless steel. The formation of stem trials which have broaching teeth formed on their outer surface from such materials is well known.

Figure 2:
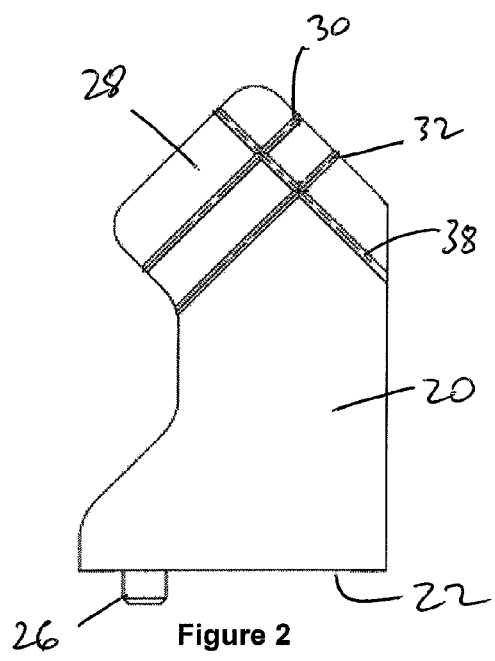
FIG. 2 is a side view of the guide portion of the trial implant.
Figure 3:
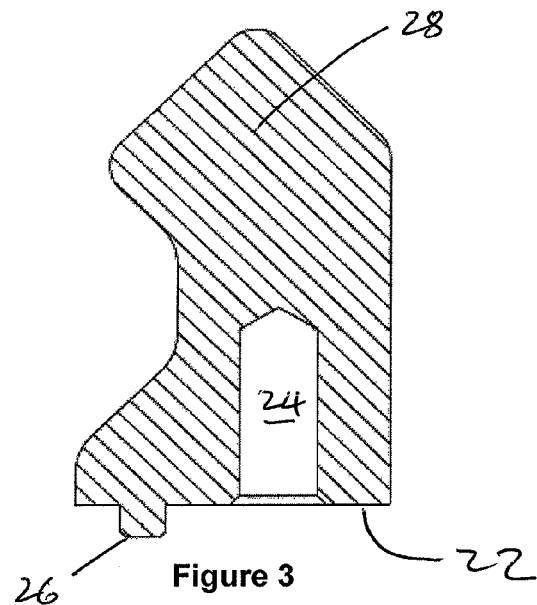
FIG. 3 is a sectional elevation through the guide portion.
Figure 4:
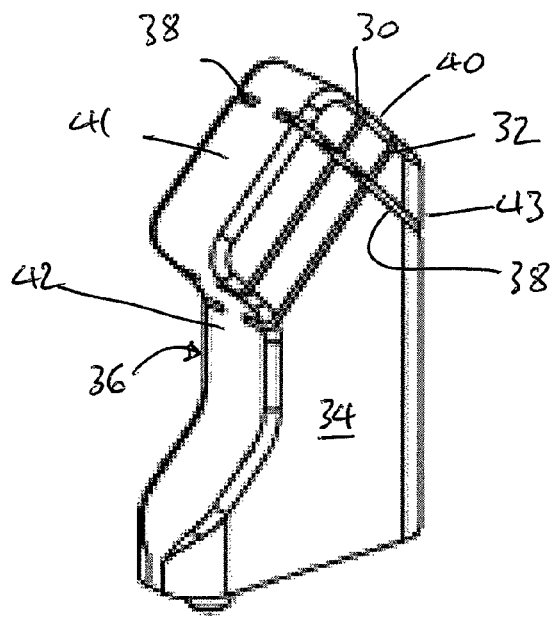
FIG. 4 is an isometric view of the guide portion.

The trial implant includes a guide portion 20 that fits on to the stem trial 10. FIGS. 2 through 4 show the guide portion in greater detail. The guide portion has a mating surface 22 that fits against the neck surface 18 on the stem trial. The mating surface on the guide portion has a first socket 24 formed in it that can receive with a sliding fit a first spigot on the neck surface of the stem trial. The mating surface of the guide portion has a second spigot 26 formed on it that can be received with a sliding fit in a corresponding second socket on the neck surface of the stem trial. The axes of each of the first socket 24 and the first spigot 26 are perpendicular to the neck surface of the stem trial. The first socket and the first spigot are spaced apart on the neck surface of the stem trial. The first spigot and the first socket are longer than the second spigot and the second socket to facilitate alignment of each of the spigot and socket pairs. The first spigot can be tapered towards its tip to facilitate insertion into the first socket. The stem trial and the guide portion are located positively relative to one another against translation and rotation when each of the spigots is received in its corresponding socket and the mating surface 22 on the guide portion abuts the neck surface 18 on the stem trial.

The guide portion 20 has a neck portion 28 that extends in a direction approximately perpendicular to the mating surface 22. The neck portion has first and second horizontal grooves 30, 32 formed in it, on each of its principal opposite faces 34, 36. Each of the first and second horizontal grooves lies in a plane, the plane of the first horizontal groove being parallel to the plane of the second horizontal groove, and spaced apart from it by about 4.8 mm. The plane of each of the first and second horizontal grooves is arranged at an angle of 45° to the mating surface 22. This means that, when the guide portion 20 is mounted on the stem trial 10, with the mating surface 22 on the guide portion abutting the neck surface 18 on the stem trial, the plane of each of the first and second horizontal grooves is approximately perpendicular to the stem axis 16.

The neck portion 28 has a vertical groove 38 formed in it, on each of its principal opposite faces 34, 36. The vertical groove intersects each of the first and second horizontal grooves 30, 32 and is perpendicular to each of them. This means that, when the guide portion 20 is mounted on the stem trial 10, with the mating surface 22 on the guide portion abutting the neck surface 18 on the stem trial, the plane of the vertical groove is approximately parallel to the stem axis 16.

Each of the horizontal and vertical grooves 30, 32, 38 has a thickness of 0.7 mm. Each of the grooves has a depth cut into the guide portion of 3.5 mm. Each of the grooves is open at each of its ends where the groove intersects the end faces 40, 41, 42, 43 of the guide portion.

The guide portion 20 can be formed from a metal such as a stainless steel or from a polymeric material such as a polyolefin, a polycarbonate, a PEEK, a polyamide, or a polyester. It can be formed by techniques that include, for example, one or more of molding and machining.

The assembly of the invention includes a plane guide 44 which is formed from a sheet of stainless steel. The plane guide is of a sufficient size that it extends from the guide portion 20 at least as far as the greater trochanter 8, as shown in FIG. 1. The thickness of the plane guide is slightly less than the thickness of each of the horizontal and vertical grooves 30, 32, 38 so that the plane guide is a snug fit in the grooves. In particular, the snug fit of the plane guide in a selected groove is such that the portion of the plane guide that extends beyond the groove is substantially fixed relative to the portion of the plane guide that is located in the groove against movement out of the plane defined by the groove.

Figure 5:
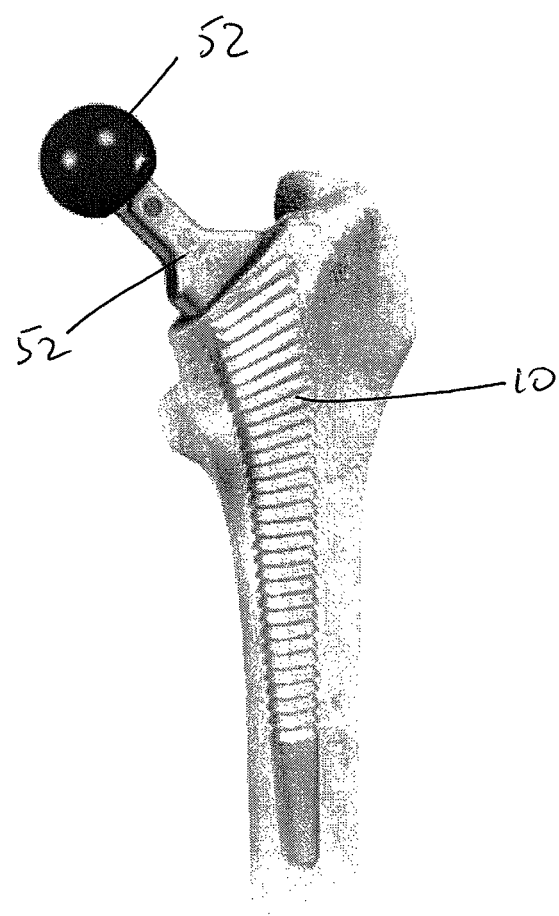
FIG. 5 is a side view of the proximal femur with a trial implant that comprises a stem located within the intramedullary cavity with a trial neck and a trial head fitted to it.

FIG. 5 shows a proximal femur 2 with a trial implant that comprises a stem trial 10 located within the intramedullary cavity with a trial neck 50 and a trial head 52 fitted to it. The trial neck has a mating surface with a spigot and a socket formed on it, which cooperate with the spigot and the socket on the neck surface 18 of the stem trial so that the stem trial and the trial neck are located positively relative to one another against translation and rotation when each of the spigots is received in its corresponding socket and the mating surface on the neck portion abuts the neck surface 18 on the stem trial.

The femur is prepared for receiving the trial instrument of the invention using techniques that are commonly used in hip replacement surgical procedures. These can include:

1. Pre-operative planning using X-ray or other images of the patient's bone structure to identify provisionally the size and type of the implant components that are to be implanted, and the required location of each implant component relative to anatomical landmarks.

2. Resecting the femoral neck at a level identified during the pre-operative planning step with reference to the X-ray images. The angle of the resection plane relative to the femoral axis will be selected according to the configuration of the intended femoral component. For many implant components, the angle between the resection plane and the femoral axis will be 45°. It can be preferred to resect the neck at a level which is slightly above the final intended level so that the bone can be finished on the final plane using a reamer.

3. Shaping the femoral canal using appropriate cutting tools such as osteotomes, rongeurs, reamers and broaches.

4. Compacting the cancellous bone in the femoral canal using one or more impactors and one or more broaches.

5. With the largest of the broaches left in place within the bone cavity, finishing the resected bone in the femoral neck using a calcar reamer, using the broach as a guide for the height and orientation of the reamer. This step defines the bearing plane for a collared stem component which is ultimately to be implanted.

6. The guide portion of the trial implant is fitted to the stem trial. The guide portion is used to assess the position of the stem trial relative to adjacent anatomical landmarks such as the lesser trochanter, the trochanteric fossa and the greater trochanter using a plane guide, fitted into the grooves on the guide portion of the trial implant. If the position of the stem trial relative to the anatomical landmark is not correct, it might then be appropriate to work further on shaping the bone cavity (using conventional cavity shaping techniques) until the trial implant can be positioned correctly.

7. The guide portion is removed from the trial implant and is replaced by the trial neck with the trial head, which can then be used to assess range of motion of the of the joint using an appropriate corresponding acetabular trial.

Subsequent steps in the procedure involve removal of the trial components and implantation of implant components using techniques which are conventional in hip joint replacement procedures.

What is claimed is:

1. A trial instrument assembly for use in a surgical procedure to replace an orthopaedic joint, the assembly comprising:
   a. a trial implant having a stem portion for fitting within a prepared cavity in the patient's bone, the stem portion defining a stem axis, and a neck portion that is connected to the stem portion at a mating surface and to protrude from the cavity when the stem portion is disposed within the cavity; and
   b. a plane guide that extends from the neck portion in a plane that is selected from (i) a plane perpendicular to the stem axis, and (ii) a plane parallel to the stem axis; wherein the plane guide is a sheet of material;
   wherein the neck portion includes a first groove and a second groove, the first groove arranged at an angle of about 45° from the mating surface and the second groove being perpendicular to the first groove and the neck portion includes a projection adapted to engage one of the first and second grooves.

2. The assembly of claim 1, wherein the plane guide includes a projection being received within one of the first and second grooves.

3. The assembly of claim 2, wherein the projection and first and second grooves assembly comprise a tongue and a groove, in which the tongue can be received in the groove to connect the plane guide with the trial implant.

4. The assembly of claim 1, wherein the stem and neck portions of the trial implant are provided as separate components that comprise formations by which the components can be connected to one another.

5. The assembly of claim 1, wherein the stem portion of the trial implant has an external surface and at least one cutting tooth formed on the external surface.

6. The trial instrument assembly of claim 1, wherein the neck portion of the trial implant includes a third groove parallel to the first groove.

7. A trial instrument assembly for use in a surgical procedure to replace an orthopaedic joint, the assembly comprising: a trial implant having a body portion for fitting within a prepared cavity in the patient's bone and a guide portion that is connected to the body portion at a mating surface to protrude from the cavity when the body portion is disposed within the cavity, the guide portion providing a first groove and a second groove, the first groove arranged at an angle of about 45° from the mating surface and the second groove being perpendicular to the first groove, at least one of the first and second grooves; and a plane guide having a first portion that provides a projection adapted to engage at least one of the first and second grooves, and a second portion that, when the projection is engaged with the at least one of the first and second grooves, extends beyond the first portion, wherein the plane guide is a sheet of material.

8. The assembly of claim 7, wherein the body and guide portions of the trial implant are provided as separate components that have formations by which the said components can be connected to one another.

9. The assembly of claim 8, wherein the formations comprise at least one spigot provided on one of the components and a corresponding socket on the other of the components in which the spigot can be received.

10. The assembly of claim 7, further comprising a trial neck component that can be fitted to the body portion of the trial implant in place of the guide portion of the trial implant.

11. The assembly of claim 7, wherein the body portion of the trial implant is a stem trial for use in preparing the femur in a hip joint replacement procedure or for use in preparing the humerus in a shoulder joint replacement procedure.

12. The assembly of claim 7, wherein the projection defines a tongue that fits in a selected one of the grooves.

13. The trial instrument assembly of claim 7, wherein the guide portion of the trial implant includes a third groove parallel to the first groove.

\* \* \* \* \*